United States Patent [19]

Martel et al.

[11] 4,364,928

[45] Dec. 21, 1982

[54] NOVEL SALTS OF ION EXCHANGE RESINS OF THE ACID TYPE

[75] Inventors: Jacques Martel, Bondy; Jean Tessier, Vincennes; Pierre Girault, Paris; Jean A. Grandadam, Saint-Maur des Fosses, all of France

[73] Assignee: Roussel-Uclaf, Paris, France

[21] Appl. No.: 194,907

[22] Filed: Oct. 7, 1980

[30] Foreign Application Priority Data

Oct. 23, 1979 [FR] France .................................. 79 26221
Jan. 31, 1980 [JP] Japan .................................... 55-9464

[51] Int. Cl.$^3$ ........................ B01J 39/20; A61K 31/74
[52] U.S. Cl. ........................................... 424/79; 521/32
[58] Field of Search ............................ 424/79; 521/32

[56] References Cited

U.S. PATENT DOCUMENTS 3,250,623 5/1966 St. Clair .................................. 424/79
3,539,564 11/1970 Shetty .................................... 424/79

OTHER PUBLICATIONS

Chem. Abstracts, 9th Collective Edition, Quinazolone, 3[3—(3—hydroxy—2—piperidinyl)—2—oxopropyl].

*Primary Examiner*—Joseph L. Schofer
*Assistant Examiner*—Peter F. Kulkosky
*Attorney, Agent, or Firm*—Hammond & Littell, Weissenberger and Muserlian

[57] ABSTRACT

Ion exchange resins of the acid type at least partially salified with 7-bromo-6-chloro-febrifugin having very good coccidiostatic activity, a very good anti-leucocytozoonosis activity and a low toxicity and their preparation.

41 Claims, No Drawings

NOVEL SALTS OF ION EXCHANGE RESINS OF THE ACID TYPE

STATE OF THE ART 7-bromo-6-chloro-ferbrifugin is a racemic compound of the formula:

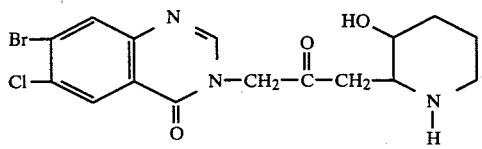

and is described in French Pat. No. 1,550,956. Its active isomers, such as its dextrorotatory isomer, are described in French Pat. No. 2,339,401. Also related is U.S. Pat. No. Re. 26,833.

OBJECTS OF THE INVENTION

It is an object of the invention to provide novel salts of acid ion exchange resins at least partially salified with 7-bromo-6-chloro-febrifugin and their preparation.

It is another object of the invention to provide novel anticoccidiostatic and anti-leucocytozoonosis compositions and to provide a novel method of protecting poultry against cocidiosis and leucocytozoonosis.

These and other objects and advantages of the invention will become obvious from the following detailed description.

THE INVENTION

The novel salts of the invention are comprised of acid ion exchange resins at least partially salified with 7-bromo-6-chloro-febrifugin. The acid groups of the ion exchange resins may be sulfonic acid, phosphonic acid or carboxylic acid, preferably sulfonic acid groups.

All sulfonic acid resins can be conveniently used to prepare the salts of the invention and useful, for example, are sulfonated polymers of polyvinylaryl monomers such as described in U.S. Pat. No. 2,366,007, especially sulfonated copolymers of styrene and divinylbenzene. Also useful are sulfonated copolymers of methacrylic acid and divinylbenzene. The invention is not limited to any category of granulometrated or reticulated resins.

Especially useful for the salts of the invention are the commercial Amberlite resins but other commercial resins with a strong acid group are also useful.

In a preferred embodiment of the invention, the acid groups of the ion exchange resins are only partially salified with 7-bromo-6-chloro-febrifugin and the other acid groups are salified with a compatible metal which will not adversely effect the animal feed such as alkali metals, alkaline earth metals, magnesium, manganese, iron, copper and zinc, preferably an alkali metal or alkaline earth metal. However, also included within the scope of the invention are the resins partially salified with manganese, magnesium, iron, copper and zinc.

Examples of alkali metals are sodium, potassium and lithium and the preferred alkaline earth metal is calcium. The preferred salts of the invention are ion exchange resins whose acid groups are partially salified with 7-bromo-6-chloro-febrifugin and partially with sodium or calcium. The preferred salts contain 1 to 20%, more preferably 5 to 10%, by weight of 7-bromo-6-chloro-febrifugin which is preferably in the racemic form.

The process of the invention for the preparation of the novel salts of the invention comprises at least partially salifying an acid ion exchange resin with 7-bromo-6-chloro-febrifugin and recovering the resulting salt. In a preferred mode of the process, an acid ion exchange resin is salified with an alkali metal to obtain an acid salt which is the reacted with 7-bromo-6-chloro-febrifugin to obtain a mixed alkali metal and 7-bromo-6-chloro-febrifugin salt of the acid resin which, if desired, may be reacted with a salified non-alkali metal salt to obtain the mixed non-alkali metal and 7-bromo-6-chloro-febrifugin salt of the acid resin. The preferred non-alkali metals are alkaline earth metals, manganese, magnesium, iron, copper and zinc.

The novel salts of the invention may be obtained by adding the optionally salified acid ion exchange resin to a solution of 7-bromo-6-chloro-febrifugin or a salt of 7-bromo-6-chloro-febrifugin with an acid or by passing a solution of 7-bromo-6-chloro-febrifugin through a column containing the optionally salified acid ion exchange resin. Therefore, by modifying the type or quantity of resin, one can adjust the proportion of 7-bromo-6-chloro-febrifugin in the obtained salt so that the value that one desired to obtain may be as much as desired provided that the value is within the capacity of the ion exchange resin used.

In a preferred mode of the invention, the solvent for 7-bromo-6-chloro-febrifugin is water or an organic solvent such as methanol, ethanol, acetone or chloroform as long as the solvent does not destroy the capacity of the exchange ions of the resin. Water is the preferred solvent. The preferred acid ion exchange resins are the sulfonic acid types. The preferred salt of 7-bromo-6-chloro-febrifugin with an acid is with hydrobromic acid or hydrochloric acid.

In a preferred embodiment of the process, an acid ion exchange resin salified with an alkali metal is reacted with a salt of 7-bromo-6-chloro-febrifugin to obtain a mixed alkali metal and 7-bromo-6-chloro-febrifugin salt of the acid ion exchange resin which, if desired, may be reacted with a soluable alkaline earth metal salt to obtain the mixed alkaline earth metal and 7-bromo-6-chloro-febrifugin salt of the acid ion exchange resin.

Preferably, the resin is a sulfonic acid ion exchange resin salified with sodium and it is reacted with 7-bromo-6-chloro-febrifugin hydrobromide to obtain the mixed sodium and 7-bromo-6-chloro-febrifugin salt of the resin which may, if desired, be reacted with calcium chloride to obtain the mixed calcium and 7-bromo-6-chloro-febrifugin salt of the sulfonic acid resin.

The anti-leucocytozoonosis and coccidiostatic compositions of the invention are comprised of an anti-leucocytozoonosically and coccidiostatially effective amount of at least one acid ion exchange resin at least partially salified with 7-bromo-6-chloro-febrifugin and an inert carrier. The composition may be in the form of powders, tablets, coated tablets, cachets, capsules, granules, emulsions or syrups prepared in a known manner.

Examples of suitable carriers or excipients are talc, arabic gum, lactose, starch, magnesium stearate, aqueous or non-aqueous vehicles, fatty bodies of animal or vegetable origin, paraffinic derivatives, glycols, diverse wetting agents, dispersants and emulsifiers and preservatives.

The compositions of the invention are useful to protect poultry, sheep and bovines against coccidosis and poultry against leucocytozoonosis.

The compositions of the invention may also be incorporated into the alimentary compositions of the animals which contain at least one salt of the invention associated with a nutritive mixture adapted for the animal feed. The nutritive mixture can be varied for the animal species to be treated and may include cereals, sugars, and grains, soya press cake, peanuts and turnsole, a flour of animal origin such as fish flour, amino acids, mineral salts, vitamins and antioxidants.

The dosage for addition to animal feeds comprises 5 to 100 parts per million of the novel salts of the amount of feed to be ingested by the animal. The dosage is for example between 100 and 20,000 $\gamma$ of active product for chickens eating between 20 and 220 g of feed per day.

The novel method of the invention for protecting poultry, sheep and bovines against coccidiosis and poultry against leucocytozoonosis comprises administering to said farm animals an effective amount of at least one salt of the invention.

In the following examples there are described several preferred embodiments to illustrate the invention. However, it should be understood that the invention is not intended to be limited to the specific embodiments.

EXAMPLE 1

Mixed sodium and 7-bromo-6-chloro-febrifugin salt of a sulfonic acid resin

A mixture of 100 g of Amberlite IRP 69 resin in the sodium salt form, one liter of water and 10 g of racemic micronized 7-bromo-6-chloro-febrifugin hydrobromide was stirred at 20°–25° C. for 16 hours and was then vacuum filtered. The recovered product was washed with water and dried to obtain mixed sodium and 7-bromo-6-chloro-febrifugin salt of a sulfonic acid resin titrating 8.8% by weight of 7-bromo-6-chloro-febrifugin (salt I).

EXAMPLE 2

Mixed calcium and 7-bromo-6-chloro-febrifugin salt of sulfonic acid resin

A mixture of 500 ml of distilled water, 20 g of the product of Example 1 and 20 g of calcium chloride was stirred at 20°14 25° C. for 20 hours and was then filtered. The recovered product was washed with water until halogen did not appear in the wash water and was dried to obtain 20 g of mixed calcium and 7-bromo-6-chloro-febrifugin salt of sulfonic acid resin titrating 7.9% by weight of 7-bromo-6-chloro-febrifugin (salt II).

EXAMPLE 3

A mixture of 35 g of Amberlite IRP 69 resin in its sodium form, 10 g of 7-bromo-6-chloro-febrifugin hydrobromide and one liter of water was stirred at 20° C. for 16 hours and was then filtered. The recovered product was washed with water and dried to obtain 32 g of the mixed sodium and 7-bromo-6-chloro-febrifugin salt of the said sulfonic acid resin.

A mixture of 32 g of calcium chloride, 700 ml of distilled water and 32 g of the said mixed salt was stirred for 23 hours and was then filtered. The recovered product was washed with water and dried to obtain 32.1 g of the mixed calcium and 7-bromo-6-chloro-febrifugin salt of the said sulfonic acid resin titrating 19.8% by weight of 7-bromo-6-chloro-febrifugin (salt III).

EXAMPLE 4

Using the procedure of Example 3, 100 g of Amberlite IRA 69 in the sodium salt form, 10 g of 7-bromo-6-chloro-febrifugin hydrobromide and one liter of water were reacted to obtain the mixed sodium and 7-bromo-6-chloro-febrifugin salt of the said sulfonic acid resin. The latter mixed salt was then reacted with 100 g of calcium chloride to obtain a mixed calcium and 7-bromo-6-chloro-febrifugin salt of the said resin titrating 8.4% of 7-bromo-6-chloro-febrifugin (salt IV).

EXAMPLE 5

Using the procedure of Example 3, 50 g of Amberlite IRP 69 in its sodium salt form, 1000 ml of distilled water and 10 g of 7-bromo-6-chloro-febrifugin hydrobromide were reacted to form the mixed sodium and 7-bromo-6-chloro-febrifugin salt of the said resin. The mixed salt was reacted with 50 g of calcium chloride to obtain the mixed calcium and 7-bromo-6-chloro-febrifugin salt of the said resin titrating 16% by weight of 7-bromo-6-chloro-febrifugin (salt V).

EXAMPLE 6

2.3 g of the sodium salt of cationic resin CS 120 (sulfonic acid copolymer of styrene and divinylbenzene containing 14% of divinylbenzene and having an exchange capacity of 4 mg equivalent per g of resin) were added to 61 ml of an aqueous solution of 0.22% of 7-bromo-6-chloro-febrifugin hydrobromide and the mixture was stirred at room temperature for 3 hours and was filtered. The resulting product was washed with water and dried to obtain 2.2 g of the mixed sodium and 7-bromo-6-chloro-febrifugin salt of the said resin titrating 5.99% by weight of 7-bromo-6-chloro-febrifugin (salt VI).

EXAMPLE 7

5 g of ion exchange resin AXT 1S in its sodium salt form (sulfonic acid copolymer of styrene-divinylbenzene of the porous type containing 20% of divinylbenzene having an exchange capacity of 0.4 mg of equivalent per g of resin) and a 102 ml of an aqueous solution of 0.27% 7-bromo-6-chloro-febrifugin hydrobromide were passed therethrough 3 times. The mixture was filtered and the recovered product was washed with water and dried to obtain 5 g of the mixed sodium and 7-bromo-6-chloro-febrifugin salt of the said resin titrating 4.6% by weight of 7-bromo-6-chloro-febrifugin (salt VII).

The same salt was prepared by adding 15 g of the said resin to 230 ml of a methanolic solution of 0.3% of 7-bromo-6-chloro-febrifugin and stirring the mixture for 5 hours at room temperature and filtering the same. The product was washed and dried to obtain 15 g of the said mixed salt titrating 4.6% by weight of 7-bromo-6-chloro-febrifugin.

EXAMPLE 8

11 g of a cation exchange resin IRP 88 in its sodium salt form (copolymer of methacrylic acid and divinylbenzene containing 15% of divinylbenzene having an exchange capacity of 4.4 mg of equivalent per g of resin) were added to 400 mg of an aqueous solution of 0.2% of 7-bromo-6-chloro-febrifugin hydrobromide and the mixture was stirred for 4 hours at room temperature and was then filtered. The recovered product was washed with water and dried to obtain 11 g of the mixed sodium and 7-bromo-6-chloro-febrifugin salt of the said resin titrating 6.08% by weight of 7-bromo-6-chloro-febrifugin (salt VIII).

EXAMPLES 9 to 12

Using the procedure of Example 8, the resins of Table I and 7-bromo-6-chloro-febrifugin hydrobromide were reacted to obtain the corresponding mixed salts of Table I.

TABLE I

| Example | Salt | Cation exchange of resin use | Process use | % of 7-bromo-6-chloro febrifugin |
|---|---|---|---|---|
| 9 | IX | exchange capacity of 4.4 mg/g CG 120 sulfonic resin | mixture | 5.46 |
| 10 | X | exchange capacity of 0.4 mg/g AXT 1S sulfonic resin | column | 6.24 |
| 11 | XI | exchange capacity of 4.4 mg/g IRP 88 carboxylic resin | mixture | 5.15 |
| 12 | XII | exchange capacity of 4.4 mg/g CG 120 sulfonic resin | mixture | 7.12 |

EXAMPLE 13

80 g of the salt of Example 1 were incorporated into sufficient excipient based on calcium carbonate to obtain a final weight of 1000 g and the resulting composition was added at the rate of 500 g per ton of complete animal feed.

COCCIDIOSTATIC ACTIVITY

The coccidiostatic activity of the salt of Example 1 was determined on groups of 20 chickens 4 weeks old and the day before infestation, the chickens were given an alimentary ration containing or not containing the product of Example 1. On day J, the chickens were infested with strain sensitive Eimeria tenella coccidies and a control group was not infected. On day J+7, the chickens were weighed and killed. The coecaux were removed, opened and washed and the lesions were noted, account being taken of the coecal contents (consistency, presence or absence of hermorrhages) according to the following scale:

Mark 0: No lesion:normal coeca.

Mark 1: presence of petechiae on the coecal mucous membrane.

Mark 2: hemorrhaging coecal mucous membrane, slightly thickened, coeca of normal size.

Mark 3: hemorrhaging coecal mucous, membrane thickened, shortened coeca. The results are reported in Table II.

TABLE II

| | healthy controls | contaminated controls | chickens which received 43 mg/kg of salt I |
|---|---|---|---|
| No. of lesions | 0 | 2.7 | 0.05 |

The results of Table I show that salt I is very active against coccidiosis. At the end of a week of treatment, the infested animals returned to normal.

Anti-Leucocytozoonosis Activity

In this test, groups of 20 young White Leghorn Cocks 50 days old were experimentally infested by oral administration of 300 units per cock of Leucocytozoon Caulleryi sporulated oocytes directly in the jabot. The animal feed was prepared not containing any preventitive agent against leucocytozoonsis except for determined quantities of the salts of the invention set forth in Table III expressed in ppm.

Between the start of the test by administration of the test salt and infestation and the end of the test, there was observed the parasitemia in the obtained blood and quantified to determine the quantity of antibodies in the serum by the precipitation test with Agar-Agar gel to determine the efficiency of the salts as preventive agents against leucocytozoonosis. The results are reported in Table III.

TABLE III

| Salt | Dose in ppm | % prevention of parasitemia | % positive tests in precipitation test |
|---|---|---|---|
| VIII | 54.6 | 1.0 | 1.5 |
| IX | 45.9 | 0 | 0 |
| X | 40.2 | 0.5 | 1.0 |
| XI | 48.7 | 0 | 0 |
| XII | 35.2 | 0.5 | 0.5 |
| Zorin 25 controls | 125 | 4.0 | 4.5 |

Acute Toxicity

The acute oral toxicity of the salt of Example 1 was determined on groups of male and female mice by the Finney method and the $DL_{50}$ dose (does which killed 50% of the animals) was determined to be 66 and 57 mg/kg on male and female mice, respectively which means that the product has a low toxicity.

The acute toxicity was determined by the Litchfield Wilcoxon method on male mice for the salts reported in Table IV.

TABLE IV

| Salt | $DL_{50}$ in mg/kg |
|---|---|
| VI | 63.0 |
| VIII | 60.8 |
| IX | 65.3 |
| XI | 67.6 |
| XII | 54.7 |

The results of Table IV show that the tested salts have a low toxicity.

Various modifications of the products and methods of the invention may be made without departing from the spirit or scope thereof and it is to be understood that the invention is intended to be limited only as defined in the appended claims.

We claim:

1. An ion exchange resin of the acid type at least partially salified with 7-bromo-6-chloro-febrifugin.

2. A resin of claim 1 wherein the acid resin is a sulfonic acid resin.

3. A resin of claim 1 wherein the resin is a polymer of a polyvinylaryl compound.

4. A resin of claim 1 wherein only a portion of the acid groups are salified with 7-bromo-6-chloro-febrifugin.

5. A resin of claim 4 wherein the acid groups not salified with 7-bromo-6-chloro-febrifugin are salified with a metal compatible with the ingredients of animal feed.

6. A resin of claim 5 wherein the said metal is selected from the group consisting of alkali metal and alkaline earth metals.

7. A resin of claim 5 wherein the metal is selected from the group consisting of manganese, magnesium, iron, copper and zinc.

8. A resin of claim 6 wherein the metal is sodium.

9. A resin of claim 6 wherein the metal is calcium.

10. A resin of claim 4 wherein the salt contains 1 to 20% by weight of 7-bromo-6-chloro-febrifugin.

11. A resin of claim 10 wherein the salt contains 5 to 10% by weight of 7-bromo-6-chloro-febrifugin.

12. A resin of claim 1 wherein 7-bromo-6-chloro-febrifugin is in the racemic form.

13. An anti-leucocytozoonosis and coccidostatic composition comprising an anti-leucocytozoonosically and coccidiostatially effective amount of at least one acid ion exchange resin at least partially salified with 7-bromo-6-chloro-febrifugin and an inert carrier.

14. A composition of claim 13 wherein the acid resin is a sulfonic acid resin.

15. A composition of claim 13 wherein the resin is a polymer of a polyvinylaryl compound.

16. A composition of claim 13 wherein only a portion of the acid groups are salified with 7-bromo-6-chloro-febrifugin.

17. A composition of claim 16 wherein the acid groups not salified with 7-bromo-6-chloro-febrifugin are salified with a metal compatible with the ingredients of animal feed.

18. A composition of claim 17 wherein the said metal is selected from the group consisting of alkali metal and alkaline earth metals.

19. A composition of claim 17 wherein the metal is selected from the group consisting of manganese, magnesium, iron, copper and zinc.

20. A composition of claim 18 wherein the metal is sodium.

21. A composition of claim 18 wherein the metal is calcium.

22. A composition of claim 16 wherein the salt contains 1 to 20% by weight of 7-bromo-6-chloro-febrifugin.

23. A composition of claim 22 wherein the salt contains 5 to 10% by weight of 7-bromo-6-chloro-febrifugin.

24. A composition of 13 wherein 7-bromo-6-chloro-febrifugin is in the racemic form.

25. A composition of claim 13 wherein the carrier is a nutritive mixture for an animal feed.

26. The method of protecting poultry, sheep and bovines against coccidiosis and poultry against leucocytozoonosis comprising administrating to said farm animals an effective amount of at least one salt of claim 1.

27. A method of claim 26 wherein the acid resin is a sulfonic acid resin.

28. A method of claim 26 wherein the resin is a polymer of a polyvinylaryl compound.

29. A method of claim 26 wherein only a portion of the acid groups are salified with 7-bromo-6-chloro-febrifugin.

30. A method of claim 29 wherein the acid groups not salified with 7-bromo-6-chloro-febrifugin are salified with a metal compatible with the ingredients of animal feed.

31. A method of claim 30 wherein the said metal is selected from the group consisting of alkali metal and alkaline earth metals.

32. A method of claim 30 wherein the metal is selected from the group consisting of manganese, magnesium, iron, copper and zinc.

33. A method of claim 31 wherein the metal is sodium.

34. A method of claim 31 wherein the metal is calcium.

35. A method of claim 29 wherein the salt contains 1 to 20% by weight of 7-bromo-6-chloro-febrifugin.

36. A method of claim 35 wherein the salt contains 5 to 10% by weight of 7-bromo-6-chloro-febrifugin.

37. A method of claim 36 wherein 7-bromo-6-chloro-febrifugin is in the racemic form.

38. A process for the preparation of a resin of claim 1 comprising at least partially salifying an acid ion exchange resin with 7-bromo-6-chloro-febrifugin.

39. The process of claim 38 wherein the acid ion exchange resin is in the form of its alkali metal salt and it is reacted with a salt of 7-bromo-6-chloro-febrifugin of an acid to obtain the mixed alkali metal and 7-bromo-6-chloro-febrifugin salt of the resin and optionally reacting the latter with a soluble non alkali metal salt to obtain the corresponding mixed non alkali metal and 7-bromo-6-chloro-febrifugin salt of the resin.

40. The process of claim 39 wherein the non alkali metal is an alkaline earth metal.

41. The process of claim 39 wherein the said ion exchange resin is a sulfonic acid ion exchange resin, the alkali metal is sodium and the acid salt of 7-bromo-6-chloro-febrifugin is the hydrobromide and the non alkali metal salt is calcium chloride.

* * * * *

UNITED STATES PATENT AND TRADEMARK OFFICE
CERTIFICATE OF CORRECTION

PATENT NO. : 4,364,928
DATED : December 21, 1982
INVENTOR(S) : JACQUES MARTEL ET AL.

It is certified that error appears in the above-identified patent and that said Letters Patent is hereby corrected as shown below:

Column 2, line 44: "soluable" should read -- soluble --.

Column 3, line 47: "20° 14 25°C" should read

-- 20°-25°C --.

Signed and Sealed this

Fifth Day of April 1983

[SEAL]

Attest:

GERALD J. MOSSINGHOFF

Attesting Officer    Commissioner of Patents and Trademarks